United States Patent
Huitema

[19]

[11] Patent Number: 6,007,497
[45] Date of Patent: Dec. 28, 1999

[54] SURGICAL BIOPSY DEVICE

[75] Inventor: Thomas W. Huitema, Cincinnati, Ohio

[73] Assignee: Ethicon Endo-Surgery, Inc., Cincinnati, Ohio

[21] Appl. No.: 09/107,845

[22] Filed: Jun. 30, 1998

[51] Int. Cl.$^6$ .................................................. A61B 5/00
[52] U.S. Cl. ........................................................ 600/567
[58] Field of Search ................................. 600/562, 565, 600/566, 567; 606/167, 170

[56] References Cited

U.S. PATENT DOCUMENTS

| | | | |
|---|---|---|---|
| 4,250,892 | 2/1981 | Dolhay et al. | 128/758 |
| 4,320,761 | 3/1982 | Haddad | 128/305 |
| 4,535,773 | 8/1985 | Yoon | 604/51 |
| 4,832,685 | 5/1989 | Haines | 604/30 |
| 4,935,005 | 6/1990 | Haines | 604/30 |
| 5,027,827 | 7/1991 | Cody et al. | 128/753 |
| 5,197,484 | 3/1993 | Kornberg et al. | 128/754 |
| 5,213,110 | 5/1993 | Kedem et al. | 128/754 |
| 5,224,470 | 7/1993 | Schnepp-Pesch et al. | 128/753 |
| 5,236,334 | 8/1993 | Bennett | 128/754 |
| 5,243,994 | 9/1993 | Ranalletta | 128/754 |
| 5,249,582 | 10/1993 | Taylor | 128/754 |
| 5,249,583 | 10/1993 | Mallaby | 128/754 |
| 5,275,609 | 1/1994 | Pingleton et al. | 606/170 |
| 5,282,476 | 2/1994 | Terwilliger | 128/753 |
| 5,284,156 | 2/1994 | Schramm et al. | 128/754 |
| 5,333,619 | 8/1994 | Burgio | 128/754 |
| 5,341,816 | 8/1994 | Allen | 128/754 |
| 5,353,804 | 10/1994 | Kornberg et al. | 128/754 |
| 5,368,045 | 11/1994 | Clement et al. | 128/754 |
| 5,394,887 | 3/1995 | Haaga | 128/754 |
| 5,400,798 | 3/1995 | Baran | 128/754 |
| 5,403,276 | 4/1995 | Schechter et al. | 604/22 |
| 5,409,013 | 4/1995 | Clement | 128/753 |
| 5,415,182 | 5/1995 | Chin et al. | 128/754 |
| 5,429,138 | 7/1995 | Jamshidi | 128/753 |
| 5,458,112 | 10/1995 | Weaver | 128/753 |
| 5,487,392 | 1/1996 | Haaga | 123/753 |
| 5,492,130 | 2/1996 | Chiou | 128/753 |
| 5,505,210 | 4/1996 | Clement | 128/753 |
| 5,507,298 | 4/1996 | Schramm et al. | 128/754 |

(List continued on next page.)

FOREIGN PATENT DOCUMENTS

| | | |
|---|---|---|
| WO 95/27443 | 4/1994 | WIPO . |
| WO 98/09561 | 6/1995 | WIPO . |
| WO 97/47243 | 6/1996 | WIPO . |

*Primary Examiner*—Max Hindenburg
*Attorney, Agent, or Firm*—Matthew S. Goodwin

[57] ABSTRACT

A biopsy probe is provided for the collection of at least one soft tissue sample from a surgical patient. The probe comprises a frame having distal and proximal ends. The probe further comprises an elongated piercing element attached to the distal end of the frame. The piercing element has a sharpened distal end for piercing tissue, and a port located proximal to the sharpened distal end for receiving a portion of tissue mass positioned adjacent to the port. The probe further includes an elongated cutter having proximal and distal ends. The cutter is disposed coaxially and slideably relative to the piercing element and has a cutting blade on the distal end for cutting the portion of tissue protruding into the port of the piercing element when the cutter slides distally past the port, thereby depositing the portion of cut tissue within the cutter lumen of the cutter proximal to the cutting blade. In one embodiment, the probe further includes a tissue remover disposed in the cutter lumen of the cutter and having a structure on the distal end for obstructing the cutter lumen so that a tissue sample protruding into the port and severed by the cutter is prevented from moving proximally through the cutter lumen. In another embodiment, the probe further comprises a distal frame seal, a proximal frame seal, and a proximal cutter seal for substantially preventing the passage of fluids through a first, a second, and a third radial space, respectively, within the probe. In a preferred embodiment, a valve is provided on the proximal end of the tissue remover for the releaseable attachment to a reservoir.

10 Claims, 11 Drawing Sheets

U.S. PATENT DOCUMENTS

| | | | |
|---|---|---|---|
| 5,526,822 | 6/1996 | Burbank et al. | 128/754 |
| 5,535,755 | 7/1996 | Heske | 128/754 |
| 5,560,373 | 10/1996 | De Santis | 128/753 |
| 5,562,102 | 10/1996 | Taylor | 128/751 |
| 5,564,436 | 10/1996 | Hakky et al. | 128/754 |
| 5,573,008 | 11/1996 | Robinson et al. | 128/754 |
| 5,595,185 | 1/1997 | Erlich | 128/754 |
| 5,603,724 | 2/1997 | O'Connor | 606/207 |
| 5,607,389 | 3/1997 | Edwards et al. | 604/22 |
| 5,615,690 | 4/1997 | Giurtino et al. | 128/754 |
| 5,643,304 | 7/1997 | Schechter et al. | 606/171 |
| 5,669,876 | 9/1997 | Schechter et al. | 604/50 |
| 5,685,838 | 11/1997 | Peters et al. | 604/22 |
| 5,685,840 | 11/1997 | Schechter et al. | 604/22 |
| 5,697,898 | 12/1997 | Devine | 604/22 |

SURGICAL BIOPSY DEVICE

This application is related to copending patent application Ser. No. 08/825,899 (Attorney Docket No. END 451) filed on Apr. 2, 1997 which is a divisional application of U.S. Pat. No. 5,649,547 (Attorney Docket No. END 449) issued on Jul. 22, 1997. This application is also related to copending application Ser. No. 08/568,143 (Attorney Docket No. END 450) filed on Dec. 6, 1995, to be issued as U.S. Pat. No. 5,769,086 on Jun. 23, 1998, and which is a continuation-in-part of U.S. Pat. No. 5,649,547.

FIELD OF THE INVENTION

The present invention relates, in general, to devices for tissue sampling and, more particularly, to improved biopsy probes for acquiring subcutaneous biopsies and for removing lesions.

BACKGROUND OF THE INVENTION

The diagnosis and treatment of patients with cancerous tumors, pre-malignant conditions, and other disorders has long been an area of intense investigation. Non-invasive methods for examining tissue are palpation, X-ray, MRI, CT, and ultrasound imaging. When the physician suspects that a tissue may contain cancerous cells, a biopsy may be done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. For a percutaneous biopsy, a needle-like instrument is used through a very small incision to access the tissue mass of interest and to obtain a tissue sample for later examination and analysis. The advantages of the percutaneous method as compared to the open method are significant: less recovery time for the patient, less pain, less surgical time, lower cost, less risk of injury to adjacent bodily tissues such as nerves, and less disfigurement of the patient's anatomy. Use of the percutaneous method in combination with artificial imaging devices such as X-ray and ultrasound has resulted in highly reliable diagnoses and treatments.

Generally there are two ways to obtain percutaneously a portion of tissue from within the body, by aspiration or by core sampling. Aspiration of the tissue through a fine needle requires the tissue to be fragmented into small enough pieces to be withdrawn in a fluid medium. The method is less intrusive than other known sampling techniques, but one can only examine cells in the liquid (cytology) and not the cells and the structure (pathology). In core biopsy, a core or fragment of tissue is obtained for histologic examination which may be done via a frozen or paraffin section.

The type of biopsy used depends mainly on various factors present in the patient, and no single procedure is ideal for all cases. Core biopsy, however, is very useful in a number of conditions and is widely used by physicians.

Due largely to heightened public awareness of the need to detect breast cancer early in its development, a number of biopsy devices for use in combination with artificial imaging devices have been commercialized. One such instrument type of biopsy instrument is the BIOPTY gun, available from C.R. Bard, Inc. and described in U.S. Pat. Nos. 4,699,154 and 4,944,308 as well as in U.S. Reissued Pat. No. 34,056. This device is spring-powered and each time a sample is to be taken, the breast or organ must be punctured again upon reinsertion of the device. Another product is the TRUE CUT needle manufactured by Travenol Laboratories. This needle collects a single core of tissue using a pointed stillete with a side-facing notch to receive tissue near its distal end and an outer, sharpened sliding cannula.

Other devices for obtaining biopsy samples from the body are described in the following: U.S. Pat. No. 5,492,130 issued to Chiou on Feb. 20, 1996; U.S. Pat. No. 5,526,821 issued to Jamshidi on Jun. 18, 1996; U.S. Pat. No. 5,429,138 issue to Jamshidi on Jul. 4, 1995; and U.S. Pat. No. 5,027,827 issued to Cody, et al, on Jul. 2, 1991. These patents describe devices which may be used for soft tissue biopsies using the aspiration method of liquid suspended tissue extraction rather than by core sampling. Numerous other devices are described in the references cited in this disclosure, and generally are for the mere removal of tissue rather than the sampling of tissue for later pathological examination.

To overcome operator error associated with such devices, and to enable multiple sampling of the tissue without having to reenter the tissue for each sample, a product now marketed under the tradename MAMMOTOME was developed. The invention which is the basis of the commercialized product is described in U.S. Pat. No. 5,526,822 issued to Burbank, et al, on Jun. 18, 1996, and is commonly owned by the assignee of the present invention. The MAMMOTOME instrument is a type of image-guided, percutaneous, coring, breast biopsy instrument. It is vacuum-assisted and some of the steps for retrieving the tissue samples have been automated. The physician uses this device to capture "actively" (using the vacuum) the tissue prior to severing it from the body. This allows for sampling tissues of varying hardness. The device can also be used to collect multiple samples in numerous positions about its longitudinal axis, and without needing to remove the device from the body. These features allow for substantial sampling of large lesions and complete removal of small ones.

Co-pending application Ser. No. 08/825,899 is a continuation-in-part of the '822 Burbank patent discussed above and describes numerous improvements to the original invention including the following: a molded tissue cassette housing permitting the handling and viewing of multiple tissue samples without physical contact by the instrument operator; the interconnection of the housing to the piercing needle using a thumbwheel to permit the needle to rotate relative to the housing, thereby preventing the vacuum tube from wrapping about the housing; several variant vacuum port embodiments; and a method for backflushing biological debris from the instrument without removing the instrument from the selected tissue location.

When using any of the devices described thus far there is a need to manage a substantial amount of different fluids either already present at the surgical site or introduced during the surgical procedure. There is some associated bleeding from the surgical site during insertion of the needle and severing of the tissue samples from the tissue mass of interest. In addition, several milliliters of local anesthetic such as lidocaine hydrochloride solution are injected into the tissue during the procedure, and there is a significant build-up of pressure inside the tissue due to the presence of the additional fluid. When the blood and anesthetic solution under this pressure within the tissue are opened to a lower or ambient pressure, the fluids will readily escape the tissue at the opening. Keeping these fluids from contaminating the patient and the instrumentation is obviously an important part of the mandatory aseptic technique, and features on the biopsy device to help accomplish this are clearly advantageous.

Coring breast biopsy devices typically incorporate an elongated piercing element to access the sampling area of the tissue mass, and a cutting cannula with a sharpened end which slides longitudinally along the piercing element. The sharpened end of the cutting cannula is driven into the tissue mass, and a core sample of the tissue is captured into the distal end of the cannula. The piercing element and/or the cannula are then withdrawn from the body and, in the case of the MAMMOTOME breast biopsy instrument, the tissue sample is transported and removed from the distal end of the cannula. This is an opportunity for fluids to escape from the tissue mass. The situation is especially acute should the biopsy device be tilted during the step of sample retrieval, as often occurs when the biopsy device is mounted on certain imaging devices. The fluids then will tend to flow "downhill" onto the devices and the surroundings.

Accordingly, what is needed is a biopsy device which can catch the fluids present during a biopsy procedure before they spill on the surroundings, and drain the fluids away to a collection cannister or the like. In addition to dealing with the backflow and gravitational effects already described, the physician also must contend with the fluids being spread by the pumping action of the relatively sliding components of the biopsy device. What is also needed, therefore, are seals advantageously mounted between the sliding components to block the spread of the fluids and to wipe the interacting surfaces clean as the device is actuated.

In the MAMMOTOME device a knockout tube is provided so that as the cutting cannula is withdrawn from the tissue and the distal end of the tube is outside the patient's body, the distal end of the knockout tube pushes out the core sample automatically from the distal end of the cutting cannula. A drain line is attached to the proximal end of the knockout tube so that fluids contained in the cutting cannula can be removed. This drain line may be attached to a vacuum source to remove the fluids more effectively. Sometimes the surgeon wishes to disconnect the drain line from the knockout tube in order to inject an additional amount of anesthetic solution into the tissue mass to insure that a sufficient amount is present at the area where the tissue sample will be taken. By removing this drain line, the fluid within the tissue which may be at a relatively high pressure can escape from the device. What is further needed, therefore, is a connecting valve on the device to allow the disconnection of the drain line, the injection of the anesthetic solution, and the reattachment of the drain line, without the loss of fluids from the tissue and onto the external surroundings. This connecting valve would also be an improvement to biopsy devices which do not have a knockout tube, but which instead have a drain line attached to the proximal end of the cutting cannula or to the proximal end of the piercing element.

SUMMARY OF THE INVENTION

The present invention is a biopsy device, sometimes referred to simply as a probe, for obtaining core samples of soft tissue while providing means to capture or contain the blood, anesthetic solution, and other fluids from within the device and the tissue mass during the surgical procedure. The proper management of fluids during the surgical biopsy procedure, as achieveable with the present invention, greatly minimizes the discomfort to the surgeon and the surgical patient, substantially prevents damage to nearby ancillary equipment, and facilitates asceptic technique during the procedure.

The probe has a frame with a distal end and a proximal end. In one preferred embodiment of the invention, a tissue sampling surface is disposed between the distal and proximal ends of the frame. In this embodiment, a drain line is attached to the frame for fluid communication with the tissue sampling surface. The tissue sampling surface is in a convenient location for retrieving the tissue sample extracted from the surgical patient. The sampling surface, together with the drain, provide an important improvement over the prior art for the collection and removal of fluids which escape from the body through the probe while retrieving the sample.

The probe also includes an elongated piercing element having a lumen, a sharpened end for piercing the tissue, and a port located proximal to the sharpened distal end for receiving a portion of a tissue mass positioned adjacent to the lateral port. The piercing element has a proximal end attached to the distal end of the frame. The probe further comprises an elongated cutter having a lumen and being disposed coaxially and slidably relative to the piercing element. The cutter has a cutting blade on the distal end for cutting the portion of tissue protruding into the port of the piercing element when the cutting blade slides distally past the lateral opening. The portion of cut tissue is deposited within the lumen of the cutter proximal to the cutting blade.

In an especially preferred embodiment, the probe includes a tubular tissue remover slideably inserted within the lumen of the cutter and having a structure disposed proximally of the port and adapted to obstruct the lumen so that a tissue sample within the cutter lumen is prevented from moving proximally. In this preferred embodiment, a valve is provided on the proximal end of the tissue remover tube and is releaseably attachable to a reservoir. The flow of air or fluids through the valve is prevented when the reservoir is not attached to it. Conversely, the flow is permitted when it is attached. The valve is also an important improvement over the prior art because of the new capability to temporarily disconnect the drain tube from the probe, inject a solution such as lidocaine hydrochloride anesthetic into the tissue through the valve, and to reconnect the drain tube to the valve, all with minimal backflow of fluids out of the probe through the valve.

In another embodiment of the present invention, there is provided a proximal frame seal to substantially prevent the passage of fluids through a first radial space between the piercing element and the distal end of the frame of the probe. Further, in a particularly preferred embodiment, a distal frame seal and a proximal cutter seal substantially prevent the passage of fluids through second and third radial spaces, respectively. The seals further facilitate fluid management during the surgical procedure by substantially preventing the leakage of the fluids from the inside of the probe.

The biopsy probe is also provided with a positioning wheel mounted on the distal end of the frame. The positioning wheel is for rotating the piercing element about its longitudinal axis, thus allowing the surgeon to extract tissue samples from around the distal end of the probe without rotating the probe frame which may be attached to drain and/or vacuum lines.

The biopsy probe of this invention where it is necessary or al procedure where it is necessary or desirable to take a biopsy tissue sample or to remove a suspected lesion. It is especially adapted for use during a minimally invasive procedure, particularly a percutaneous breast biopsy procedure.

DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
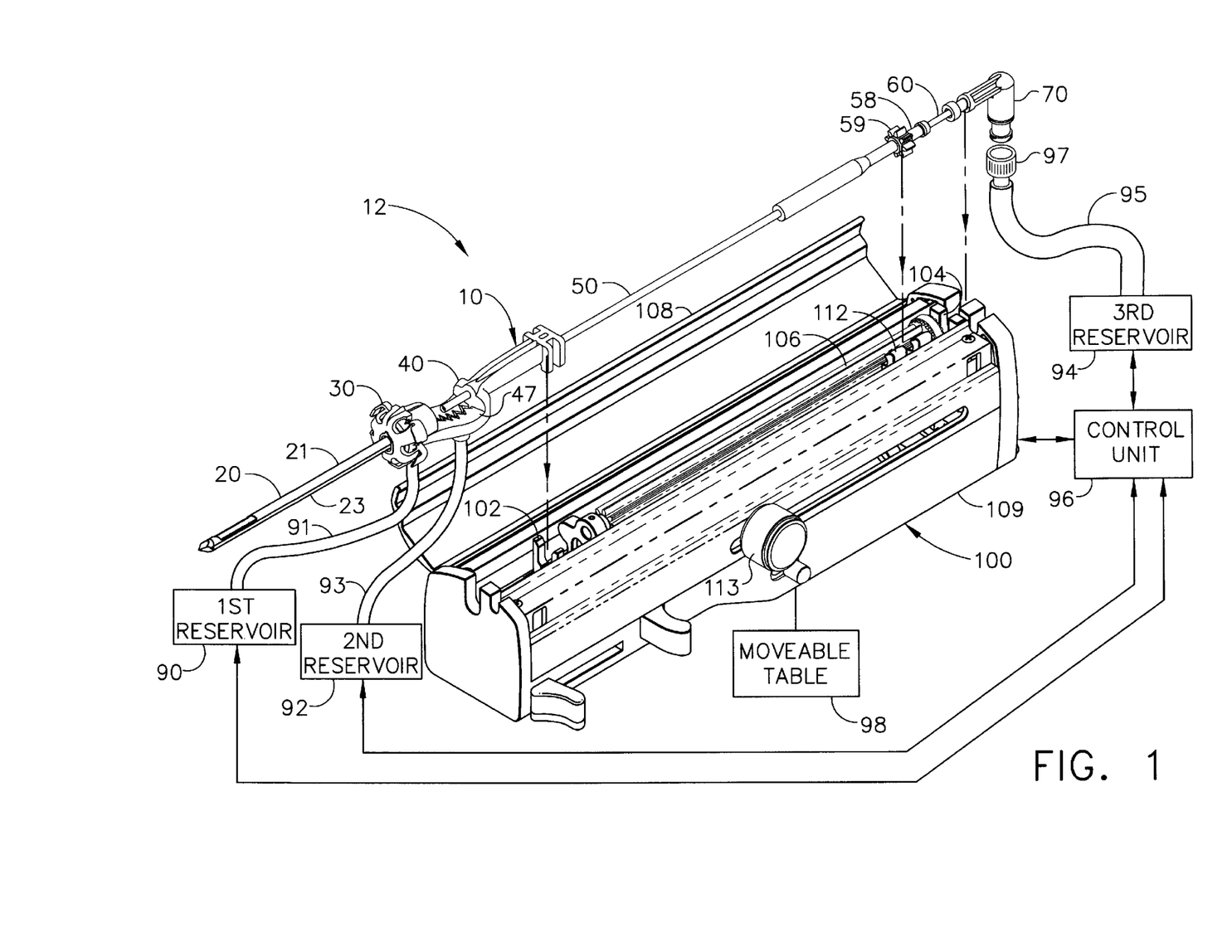
FIG. 1 is an isometric view of a biopsy apparatus, showing the biopsy probe of FIG. 2, its insertion into a driver, and schematic representations of a control unit, a plurality of vacuum sources, and a drain.

As best shown in FIG. 1, the present invention is a surgical biopsy apparatus 12, a minimally invasive type of instrument for acquiring repeated subcutaneous biopsies. In an especially preferred embodiment, the surgical biopsy apparatus 12 generally comprises a probe 10 for insertion into the tissue of the surgical patient for extraction of a tissue sample therefrom, a powered probe driver 100, a moveable table 98, a control unit 96, and a first, a second, and a third tube in fluid communication with a first, a second, and a third reservoir, respectively. In the preferred embodiment, the reservoirs 90, 92, and 94 are at least one vacuum source, although the present invention is operable without use of a vacuum source. The probe 10 of the surgical biopsy apparatus 12 is removeably mounted to the powered probe driver 100.

The driver 100 includes a housing 109 having a moveable cover 108 hingedly attached thereto. Within the housing 109 there is a housing mount fork 102 for receiving the probe 10, a cutter advance fork 112 for positioning the cutter gear 59, an elongated driver gear 106 to mate with and rotate the cutter 50. The driver 100 is attached to a moveable table 98 such as a stereotactic guidance system (not shown) for moving the probe 10 distally in order to pierce the tissue, and proximally in order to remove the probe 10 from the tissue. A cutter advance knob 113 is manually actuated to obtain the tissue sample as will be described.

The control unit 96 is used to control the sequence of actions performed by the surgical biopsy apparatus 12 in order to obtain the biopsy sample from the surgical patient. In the preferred embodiment, the control unit 96 controls the application of vacuum to the probe 10 and the activation of the cutter motor (not shown) within the driver 100. The range of vacuum pressure preferred is about 23–25 inches of mercury below atmospheric pressure.

Figure 2:
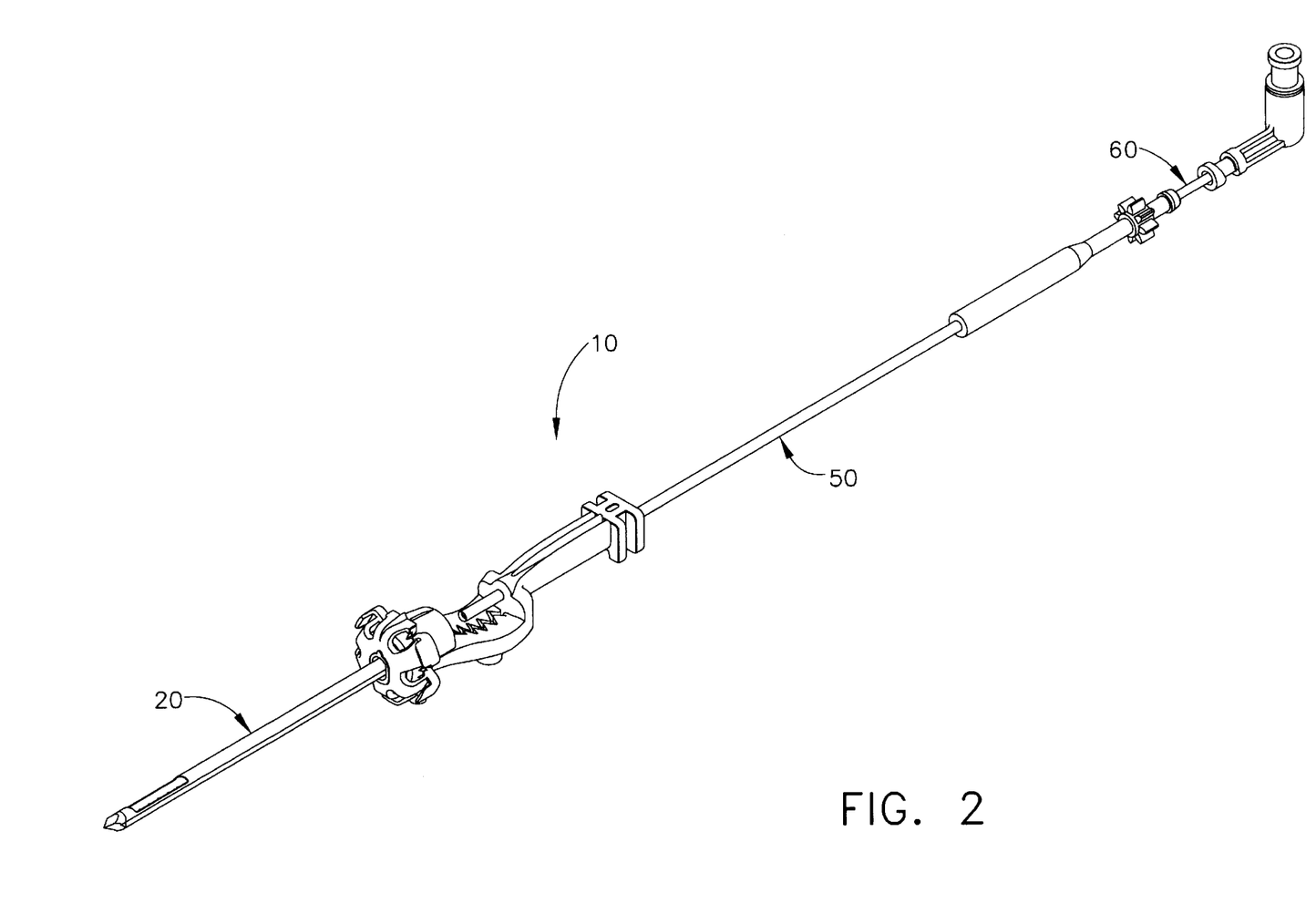
FIG. 2 is an isometric view of a preferred biopsy probe of the present invention.

FIG. 2 is an isometric view of the preferred embodiment of the probe 10 which is a coaxial assembly of three elongated elements: a piercer 20, a cutter 50, and a tissue remover 60. The tissue remover 60 is inserted slideably into the cutter 50 which, in turn, is inserted slideably into the piercing element 20. The probe 10 generally is used as follows: The skin of the surgical patient is disinfected. A local anesthetic such as lidocaine hydrochloride is injected by hypodermic needle into the tissue. A small incision is made in the skin of the surgical patient. Then the piercer 20 is placed into that incision and pierced into the tissue of the surgical patient and is advanced to the tissue area of interest by the movement of the moveable table 98. During this step the cutter 50 is completely advanced in the distal direction. Once the tissue of interest is accessed by the piercer 20, the cutter 50 is retracted in the proximal direction partway and the tissue to be extracted is drawn by vacuum into a distal end 22 of the probe 10. The cutter 50 is then actuated by the cutter motor of the driver 100 and manually advanced in the distal direction, thus severing the tissue sample captured in the distal end 22 of the probe 10. The cutter 50 is then manually retracted in the proximal direction, transporting the tissue sample to outside the patient's body. The tissue remover 60 releases or "knocks-out" the tissue sample from the cutter 50, so that the tissue sample may be retrieved for analysis.

Figure 3:
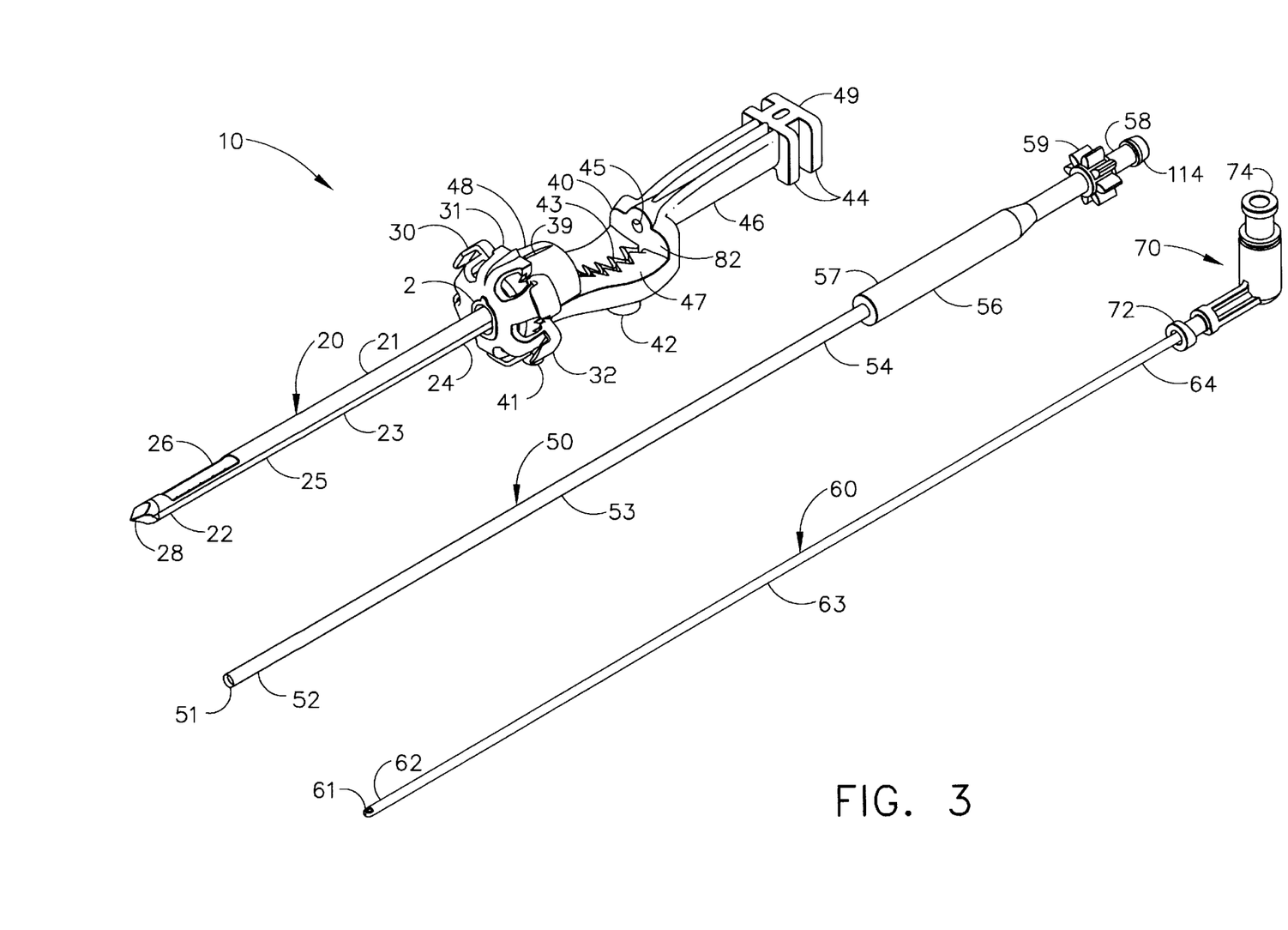
FIG. 3 is an exploded isometric view of the biopsy probe of FIG. 2.

FIG. 3 is an exploded isometric view of the probe 10, showing separately the piercer 20, the cutter 50, and the tissue remover 60. The piercer 20 comprises a frame 40 which may be made from a rigid, medical grade plastic. The frame 40 has a distal end 48, a proximal end 49, and a longitudinal axis (not shown) extending therebetween. A tubular piercing element 25 having a proximal end 24 and a distal end 22 is rotatably attached to the proximal end 48 of the frame 40 by a hub 2 (partially shown) and a positioning wheel 30. Rotation of the positioning wheel 30 by the surgeon allows positioning of a rectangular port 26 in the distal end 22 of the piercer 20. A positional indicator 31 on the wheel 30 may be referenced to a marker 39 on the frame 40 of the probe 10. By changing the position of the port 26, the surgeon may access tissue from anywhere around the distal end 22 of the piercer 20.

Piercing element 25 is preferably made from a stainless steel and includes an upper lumen 21 and a lower lumen 23. The rectangular port 26 on the distal end 22 of the piercing element 25 is located on the upper lumen 21 and is provided for receiving the tissue that is to be extracted from the surgical patient. Referring now to FIGS. 1 and 3 concurrently, the lower lumen 23 has a plurality of small holes (not shown) in the distal end 22 for the communication of the port 26 to the first reservoir 90. In the preferred embodiment, this first reservoir is a vacuum source so that the prolapse of tissue into the port 26 is greatly enhanced. The cutter 50 reciprocates axially within the upper lumen 21 as the surgeon manually operates the advancing knob 113. The piercing tip 28 is attached to the distal end 22 of the piercing element 25 and pierces into the tissue of the surgical patient by the driving force of the driver 100.

Figure 4:
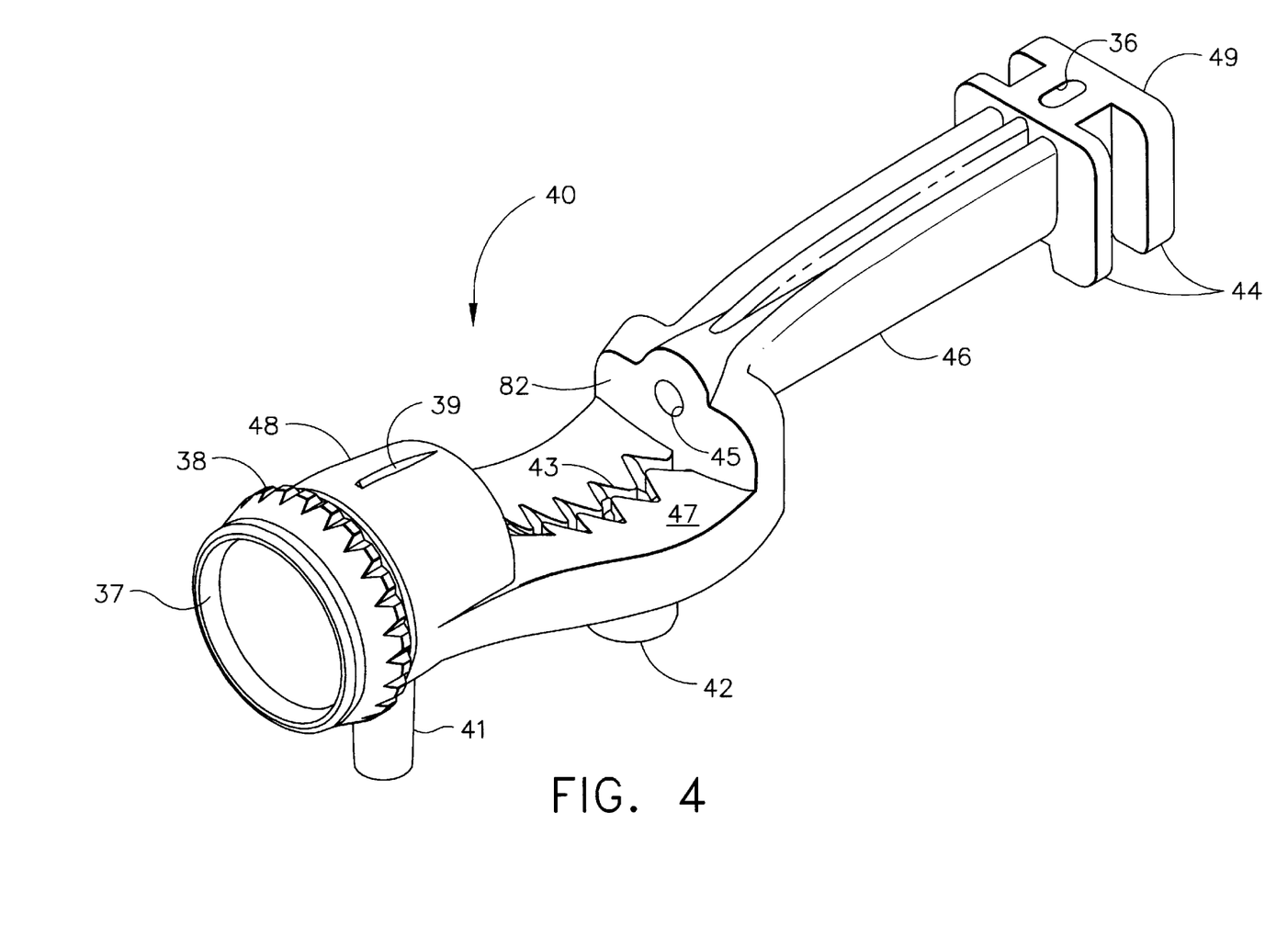
FIG. 4 is an isometric view of a probe frame of the biopsy probe of FIG. 2.
Figure 5:
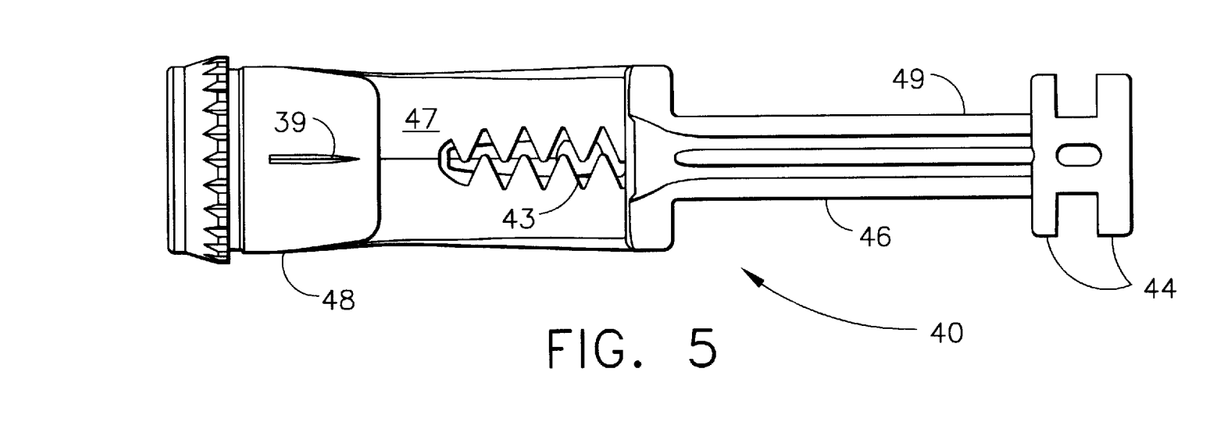
FIG. 5 is a top view of the probe frame of the biopsy probe of FIG. 2.
Figure 6:
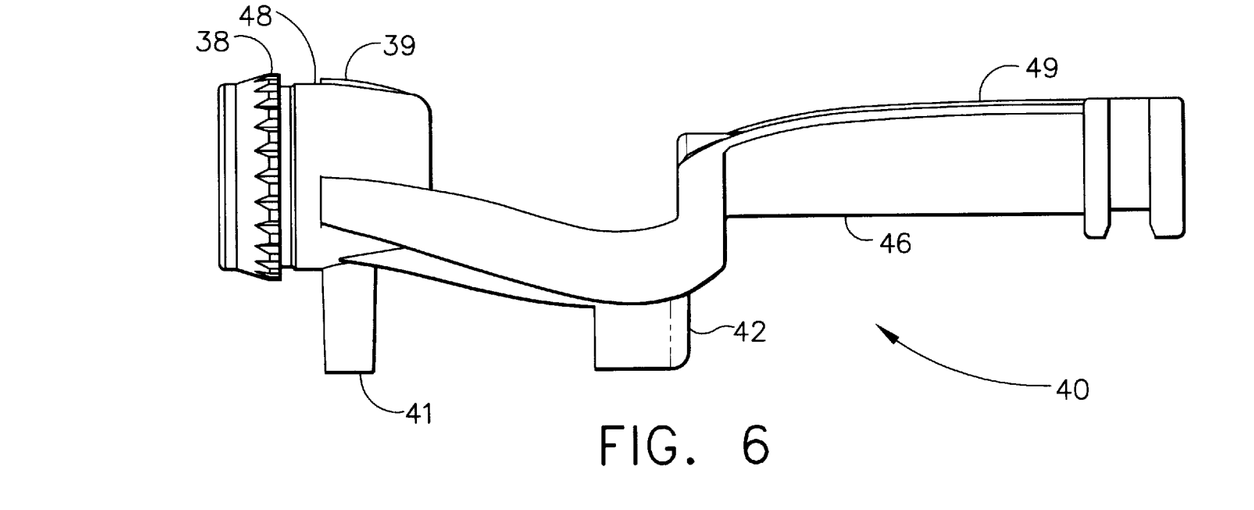
FIG. 6 is a side view of the probe frame of the biopsy probe of FIG. 2.

Referring to FIGS. 3 and 4, the frame 40 of the piercer 20 has a tissue sampling surface 47 which is where a tissue sample extracted from within the surgical patient is removed from the probe 10. Sampling surface 47 is provided with a grate 43 which connects with a drain boss 42 of the frame 40. FIGS. 4, 5, and 6 more clearly show the grate 43 and drain boss 42. The grate 43 may have many different configurations as will be apparent to those skilled in the art, but in general, the grate 43 allows the passage of fluids into the drain 92 (see FIG. 1) via the second tube 93 but prevents the tissue sample from falling into the drain boss 42. The drain boss 42 optionally may be connected to a vacuum source in order to enhance the collection of fluids from the tissue sampling area.

In FIGS. 4, 5, and 6 can also be seen a plurality of teeth 38 around the periphery of the distal end 48 of the frame 40. The teeth 38 are for interaction with the flutes 32 of the positioning wheel 30 (see FIG. 1) so that a tactile feedback is provided to the user while adjusting the location of the port 26 on the distal end 22 of the piercer 20. In addition to the tactile feedback, the teeth 38 are a holding means for the orientation of the port 26, and also a referencing means. That is, the surgeon may count the number of "detents" felt when rotating the positioning wheel 30, while looking at the relationship between the positional indicator 31 on the wheel 30 and the marker 39 on the frame 40, in order to understand the radial orientation of the port 26 on the distal end 22 of the piercer 20.

FIG. 4 shows a pair of mounting fins 44 on the proximal end 49 of the frame 40. These mounting fins 44 are removeably inserted into a mounting fork 102 of the driver 100 as depicted in FIG. 1, thus anchoring the probe 10 to the driver 100, and engaging the probe 10 to a spring-actuated firing mechanism (not visible) within the driver for instantaneously advancing the distal end 22 of the probe 10 into the tissue of the patient. This firing mechanism may be used, if desired by the surgeon, in combination with the stereotactic movement of the moveable table 98 to position the distal end 22 into the tissue of the patient.

Now referring again to FIGS. 1 and 3 concurrently, the cutter 50 comprises a distal end 52, a proximal end 58, and a longitudinal axis (not shown) extending therebetween. The cutter 50 further comprises a cutter shank 56 having a distal end 57 fixedly attached to a proximal end 54 of a hollow cutter tube 53. A longitudinal passage through the cutter shank 56 (not visible) communicates with the cutter tube 53. On the distal end of cutter tube 53 is a cutter blade 51 which is preferably made by the sharpening of the circumference of the distal end 52 of the cutter tube 53, which is preferably made of a stainless steel. On the proximal end 58 of the cutter 50 is a cutter gear 59, which is preferably integrally molded with the cutter shank 56. The cutter gear 59 is for operational engagement with an elongated gear 106 of the driver 100. When the probe 10 is inserted into the driver 100, the cutter gear 59 is positioned into the cutter advance fork 112 of the driver. The cutter advance fork 112 is attached to the cutter advance knob 113 so that movement of the knob 113 causes the like movement of the cutter 50. As the cutter 50 is moved axially by operation of the cutter advance knob 113, the cutter gear 59 moves along the elongated gear 106 of the driver 100, while maintaining operational engagement. The electric motor (not shown) of the driver rotates the cutter 50 at a preferred rate of about 1350 revolutions per minute, although the rate may vary considerably.

Figure 10:
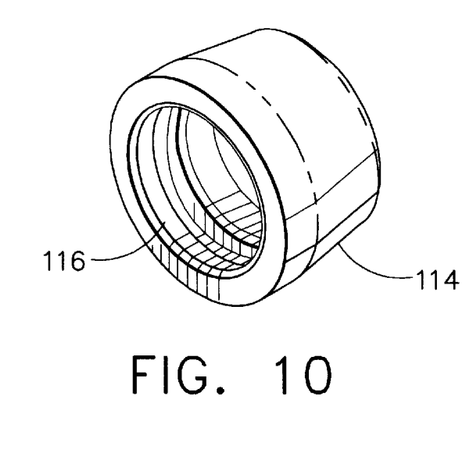
FIG. 10 is an isometric view of a proximal cutter seal which mounts on the proximal end of a cutter of the biopsy probe of FIG. 2.
Figure 11:
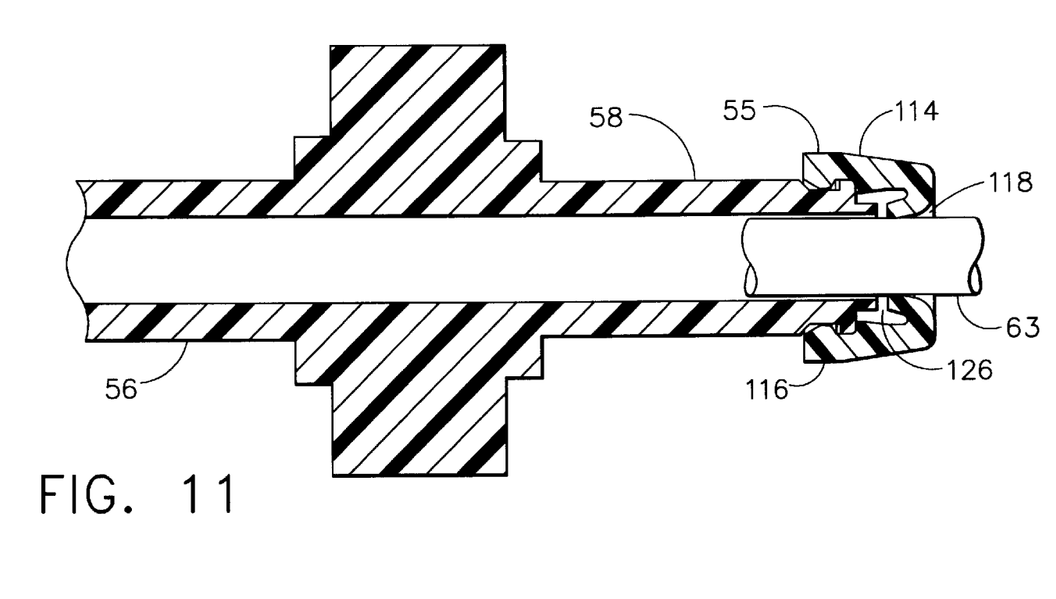
FIG. 11 is a longitudinal sectional view of the proximal portion of the cutter of the biopsy probe of FIG. 2, assembled with the proximal cutter seal of FIG. 10.

A proximal cutter seal 114 is attached to the proximal end of the cutter 50. The tissue remover 60 slides freely through the proximal cutter seal 114. The radial clearance or gap between the cutter 50 and the tissue remover 60 defines a third radial space 126 (see FIG. 11). The distal end of the cutter 50 is inside the tissue of the patient during certain portions of the operational sequence, and fluids such as blood and injected lidocaine may be under considerable pressure within the tissue. Also, the probe 12 may be tilted at an angle with respect to the earth, and fluids will tend to flow downhill (in the proximal direction) and drip/spill onto nearby instrumentation, the surgical table, and so forth. The proximal cutter seal 114 substantially prevents these fluids from escaping from the proximal end 58 of the cutter 50 through the third radial clearance 126. FIG. 10 shows an enlarged, isometric view of the proximal cutter seal 114. FIG. 11 shows the proximal cutter seal 114 retained on the proximal end 58 of the cutter shank 56. A cutter seal lip 116 elastically snaps over an annular rib 55 of the proximal end 58 of the cutter shank 56. A resilient opening 118 slideably receives and seals against a remover tube 63 of the tissue remover 60, thus substantially preventing the escape of fluids from within the cutter shank 56 through the third radial clearance 126.

The cutter tube 53 fits closely yet slides freely in a frame hole 45 which extends longitudinally through frame bushing 46 of the piercer 20. When the cutter 50 is retracted to a first position as described earlier, the cutter blade 51 of the cutter 50 is approximately adjacent to frame surface 82 of the piercer 20 so as to allow free access to the sampling surface 47 for retrieval of the tissue sample. In FIG. 1, the cutter blade 51 is shown extending about ten millimeters distal to where it would be for the first, retracted position of the cutter 50.

In FIG. 3, the tissue remover 60 comprises a remover tube 63 which has a proximal end 64, a distal end 62, and a longitudinal axis (not shown) extending therebetween. On the proximal end 64 of the remover tube 63 is attached a valve 70 having a distal end 72 , a proximal end 74 which is perpendicular to the distal end 72, and a passageway therethrough. The remover tube is hollow and preferably is made from a stainless steel. A distal tip 61 (also referred to simply as a structure) on the distal end 62 of the remover tube 63 is configured so as to allow the passage of air and fluids and to block the passage of tissue particles larger than what may pass through the tissue remover 60 and the valve 70. The distal tip 61 prevents the loss of tissue into the reservoir which may otherwise be collected for pathological analysis. The length of the remover tube 63 is such that when the cutter 50 is retracted to the first position, the distal tip 61 of the remover tube 63 is approximately adjacent to the cutter blade 51 of the cutter 50. This arrangement allows the tissue sample retrieved in the distal end 52 of the cutter 50 to be forced out of the same by the distal tip 61 of the tissue remover 60 when the cutter 50 is retracted to the first position. The tissue sample may then drop onto the tissue sample surface 47 of the piercer 10.

Figure 12:
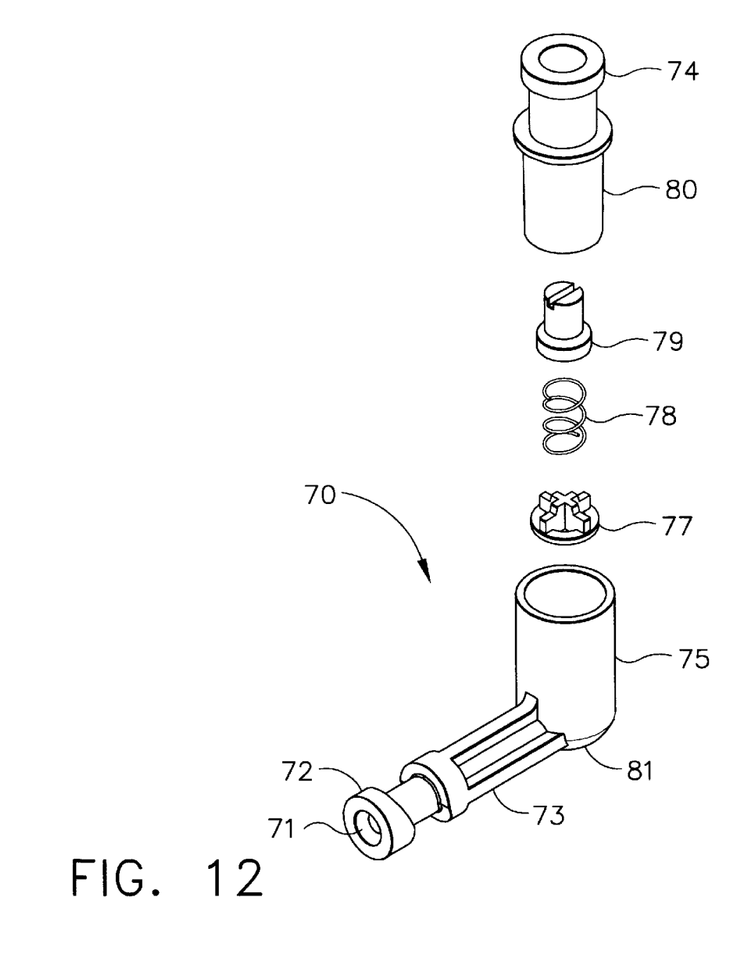
FIG. 12 is an exploded isometric view of a valve which mounts on the proximal end of a tissue remover of the biopsy probe of FIG. 2.
Figure 13:
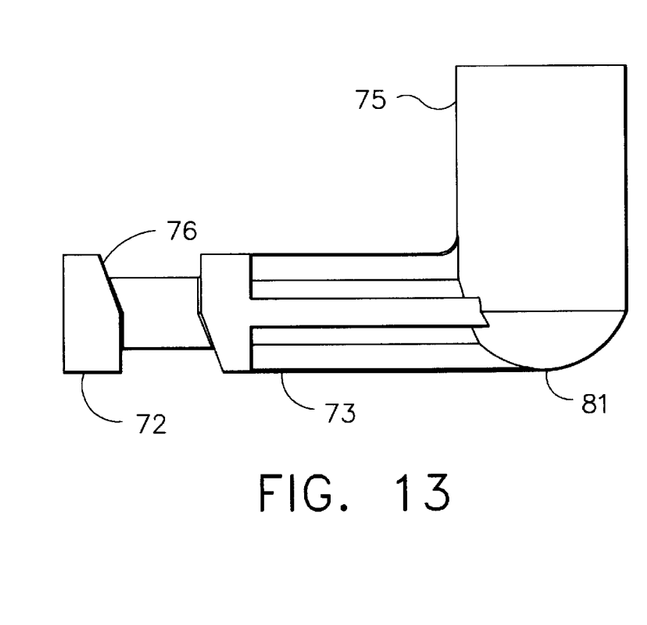
FIG. 13 is a side view of a housing of the valve of FIG. 12.
Figure 14:
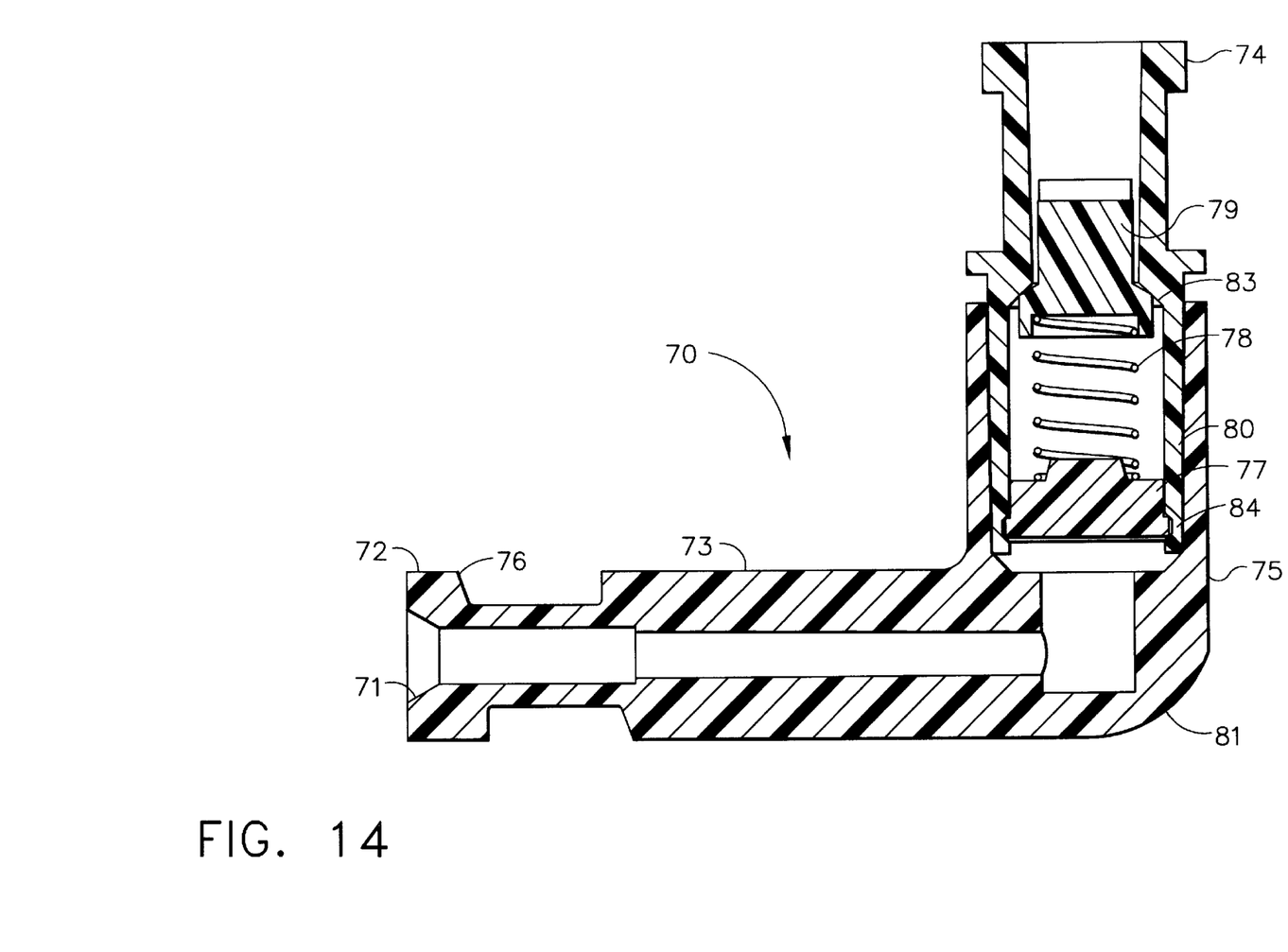
FIG. 14 is a sectional view of the valve of FIG. 12.

The valve 70 of the tissue remover 60 is shown in FIG. 12 (exploded isometric view), FIG. 13 (side view of the housing 81 only) and FIG. 14 (sectional view). The valve 70 provides for the flow of air and fluids from the tissue remover 60 to the third reservoir 95 via the third tube 95 and a connector 97 (see FIG. 1). In the preferred embodiment, the third reservoir 95 is a vacuum source which facilitates the removal of the fluids from within the probe 10, and which facilitates the transport of the tissue sample from the port 26 to the tissue sampling surface 47 (see FIG. 1). Because the tissue remover 60 is inserted into the cutter 50 which is inserted in the upper lumen 21 of the piercer 20, the vacuum source is connected to the upper lumen 21 as well and assists in drawing tissue into the port 26 prior to cutting of the tissue by the cutter blade 51. In addition to the removal of fluids from the probe 20, the vacuum provides a means of releaseably attaching the tissue sample to the end of the tissue remover 60 so that once severed, the sample may be held in the distal end 52 of the cutter tube 53 and transported from the port 26 of the piercer 20 to outside the patient's body to the tissue sampling surface 47 of the probe 10.

The valve 70 also provides a closeable port for injecting fluids into the tissue of the surgical patient. For example, as the piercing tip 28 of the probe 10 is pierced into tissue in order to access the tissue area of interest, it is common for surgeons to inject a lidocaine hydrochloride local anesthetic into the tissue through the port 26 on the upper lumen 21 of the piercer 20 via the proximal end of tissue remover tube 63 which is in fluid communication with the upper lumen 21. The valve 70 allows the surgeon to disconnect the third tube 95 from the proximal end 74 of the valve, to use a syringe to inject the lidocaine through the proximal end 74 and into the tissue, and then to remove the syringe without the lidocaine and other fluids escaping from the probe 10. Therefore, in this situation, the syringe is considered another embodiment of the third reservoir 94. The novel combination of the valve 70 with the probe 10 prevents the escape of fluids from the proximal end of the probe when neither the third tube 95 or the syringe are connected to it.

The valve 70 comprises a housing 81, a filter 77 containing small passageways therethrough (not visible), a coiled spring 78, a piston 79, and a cylinder 80. The housing 81, which is preferably made of a rigid, medical grade plastic, has a hollow stem 73 protruding perpendicularly from a bowl 75, with a communicating passageway therebetween. The distal end 72 of the valve 70 is fixedly attached to the tissue remover tube 63 as shown in FIG. 3. The bowl 75 receives the cylinder 80 which contains the spring 78, the piston 79, and the filter 77. The cylinder 80 is sealably bonded within the pipe 75 of the housing 81 by any of a number of bonding techniques well-known to those skilled in the manufacture of medical valves and the like. The assembly of the valve 70 is best shown in FIG. 14. The filter 77 is attached to the inside of the cylinder 80 in a groove 84. The filter 77 is permeable by air and fluids and provides a support for the spring 78 which biases the piston 79 against a valve seat 83 of the cylinder 80, thus preventing the escape of fluids out the proximal end 74 of the valve 70. The connector 97 (see FIG. 1) for attaching the third tube 95 to the valve 70 is adapted to releaseably attach to the proximal end 74 of the valve 70 in a manner well-known in the art as a Luer connection, so that when so connected, the piston 79 is held away from the valve seat 83, thus allowing the flow of fluids through the valve 70. When disconnected, the piston is again allowed to seal against the valve seat due to the biasing force of the spring 78 and the fluidic pressure within the valve 70. Syringes are commercially available for sealably attaching to the proximal end 74 of the valve 70. The tip of the syringe pressing on the piston 79 and/or the injection pressure of the solution coming out of the syringe is sufficient to overcome the spring 78 and to push the piston 79 away from the valve seat 83, so that the solution may flow through the valve.

Figure 15:
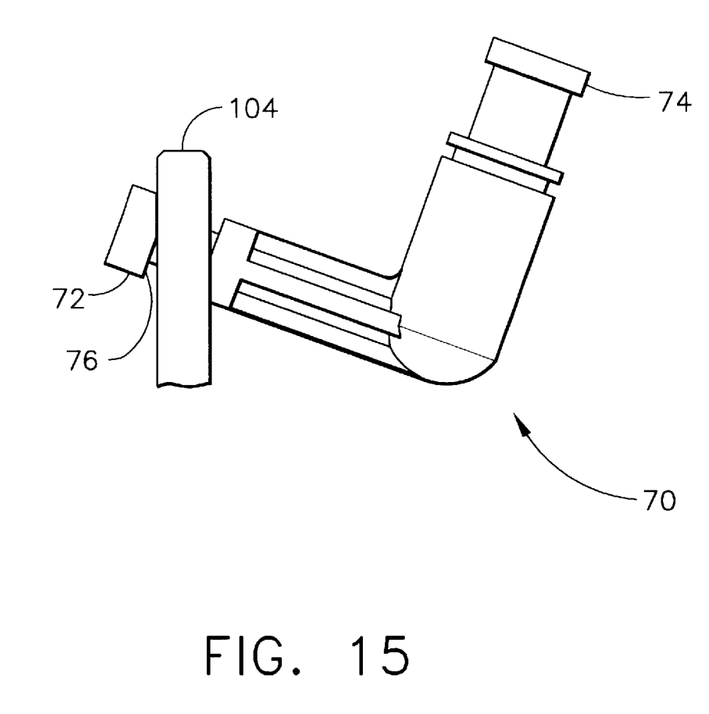
FIG. 15 is a side view of the valve of FIG. 12 as it is initially inserted into a cradle of the driver of FIG. 1, with the tissue removal tube and the drain tube removed from the valve for clarity.
Figure 16:
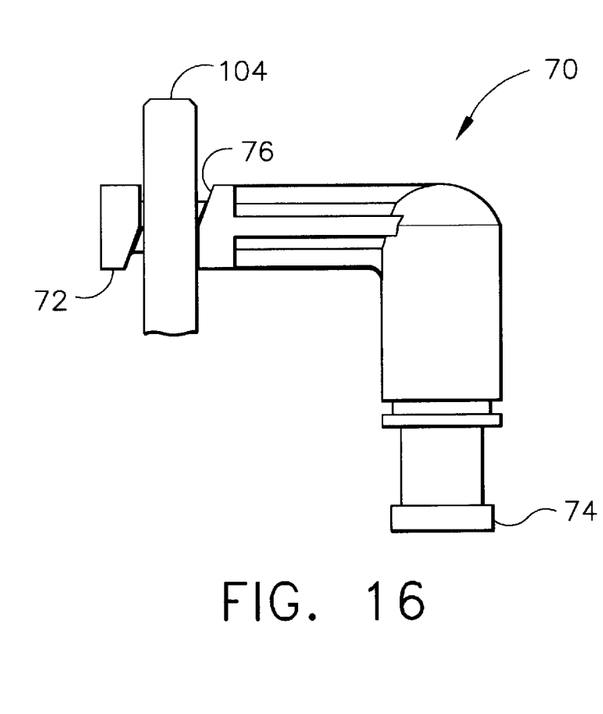
FIG. 16 is a side view of the valve of FIG. 12 as it is finally inserted into a cradle of the driver of FIG. 2, with the tissue removal tube and the drain tube removed from the valve for clarity.

In FIGS. 15 and 16, it is shown how a groove 76 on the valve 70 is used advantageously to position the valve 70 into cradle 104 of the driver 100 of FIG. 1. Of course, the valve 70 is attached to the probe 12 and to the third tube 95 on proximal end 74 of the valve when it is so positioned, but those items have been omitted from FIGS. 15 and 16 for clarity. Now referring to FIG. 15 and FIG. 1 concurrently, the valve 70 is initially lowered into the cradle 104 with the proximal end 74 of the valve oriented in the up direction. The groove 76 of the valve 70 is beveled to allow the valve to be tipped as shown, in turn allowing the distal end of the probe 12 to be lowered into the driver after the valve has been properly seated in the cradle. This tipping method of inserting the probe 12 into the driver 100 removes the necessity of having to locate the probe 12 into the mounting fork 102, the cutter advance fork 112, and the cradle 104 simultaneously. Once the entire probe 12 has been lowered into the driver, the valve 70 is rotated to the downward position as shown in FIG. 16. This results in the vacuum line 95 hanging naturally from the probe 12 in the downward direction. Axial play of the valve 70 is minimal due to the configuration of the groove 76 for mounting in the cradle 104. Minimizing the axial play of the valve 70 and the attached tissue remover 60 is important in maintaining the positional relationship of the distal tip 61 of the remover 60 to the cutting blade 51 in order to knock-out properly the tissue sample from the cutter 50 as earlier described.

Figure 7:
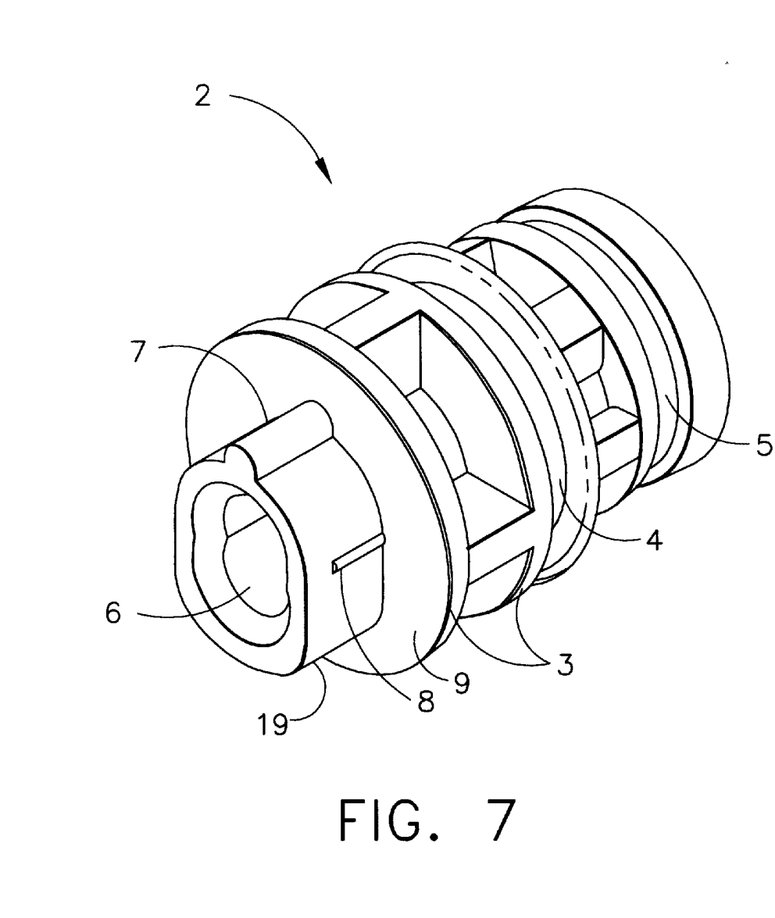
FIG. 7 is an isometric view of a distal frame seal which inserts into the distal end of the probe frame of FIG. 4.

FIG. 7 shows the hub 2 of the distal frame seal 1 in an enlarged, isometric view. As was described earlier for FIG. 3, the hub 2 is inserted into frame 40 of the piercer 20, and rotatably supports the proximal end 24 of the piercing element 25. The hub 2 of FIG. 7 comprises a first and a second O-ring seat, 4 and 5, respectively, a plurality of glands 3 for the sealable insertion into the frame 40 of the piercer 10. The hub 2 further comprises a hub step 19 extending distally from a proximal surface 9, wherein the hub step 19 is a supporting means for the positioning wheel 30 (see FIG. 3). A crush rib 8 on the hub step 19 aids in retaining the positioning wheel 30 to the hub 2. A locating projection 7 on the hub step 19 properly aligns the hub 2 with the positioning wheel 30 radially, so that the port 26 on the distal end 22 of the piercer 10 is in the up position when the marker 31 of the positioning wheel 30 is also in the up position.

Figure 9:
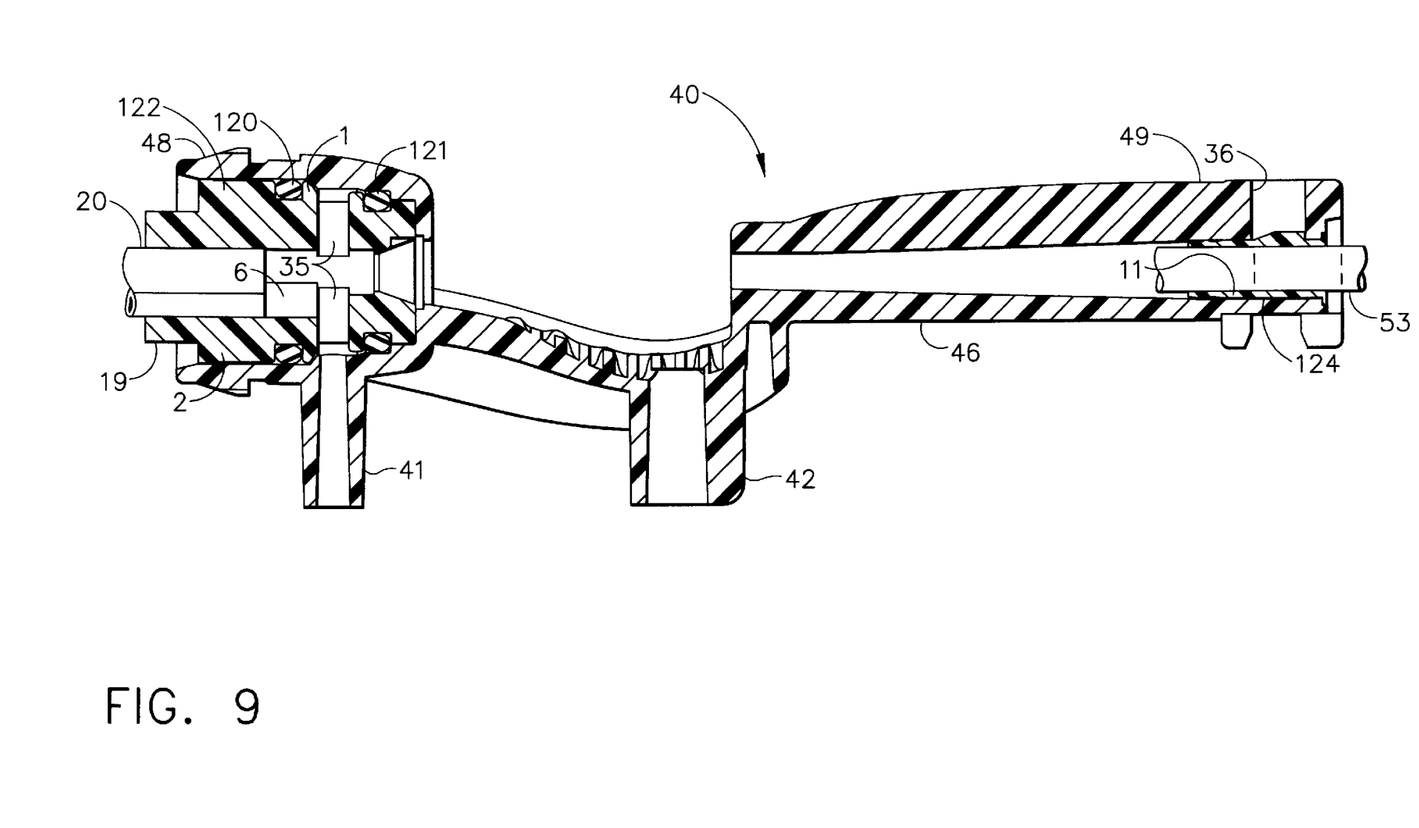
FIG. 9 is a longitudinal sectional view of the probe frame of FIG. 4 assembled with the proximal frame seal of FIG. 8 and the distal frame seal of FIG. 7.

In FIG. 9, the distal frame seal 1 is shown assembled into the distal end 48 of the frame 40. The distal frame seal 1 comprises the hub 2 and a first O-ring 120 and a second O-ring 121. A first radial space 122, which is occupied by part of the distal frame seal 1, is defined by the radial clearance between the piercing element 20 (partially shown) and the proximal end 48 of the frame 40. A lower lumen vacuum boss 41 is in alignment between the two O-rings 120 and 121 so as to allow vacuum to be delivered through passages 35 and into opening 6 of the distal frame seal 1. The first tube 91 (see FIG. 1) from the first reservoir 90 is a flexible, medical grade tube which may fit tightly over the vacuum boss 41. The proximal end 24 of the lower lumen 23 of the piercing element 25 is inserted into the opening 6 of the distal frame seal 1 so that the vacuum may be delivered through the lower lumen 23 and to the port 26 on the distal end 22 of the piercer 20.

Although not shown in FIG. 9, it can be appreciated by those skilled in the art that the connection of the first tube 91 to the vacuum boss 41 may be facilitated by any one of a number of embodiments of connectors. Such connectors may be made, for example, of a semi-rigid, medical grade elastomer such as polyurethane exhibiting improved frictional characteristics at the attachment interfaces to the vacuum boss 41 and the tube 91, as compared to when the tube is attached directly to the boss. The use of such a connector would provide an advantage to the surgeon of helping to prevent the accidental disconnection of the tube 91 from the vacuum boss 41 during the use of the present invention. Such a connector could be configured in a "L" shape or elbow so that the angle of attachment of the tube 91 with respect to the probe axis could vary by swiveling the connector upon the vacuum boss 41. This would be useful to the surgeon when positioning the probe in various orientations during the surgical procedure.

Figure 8:
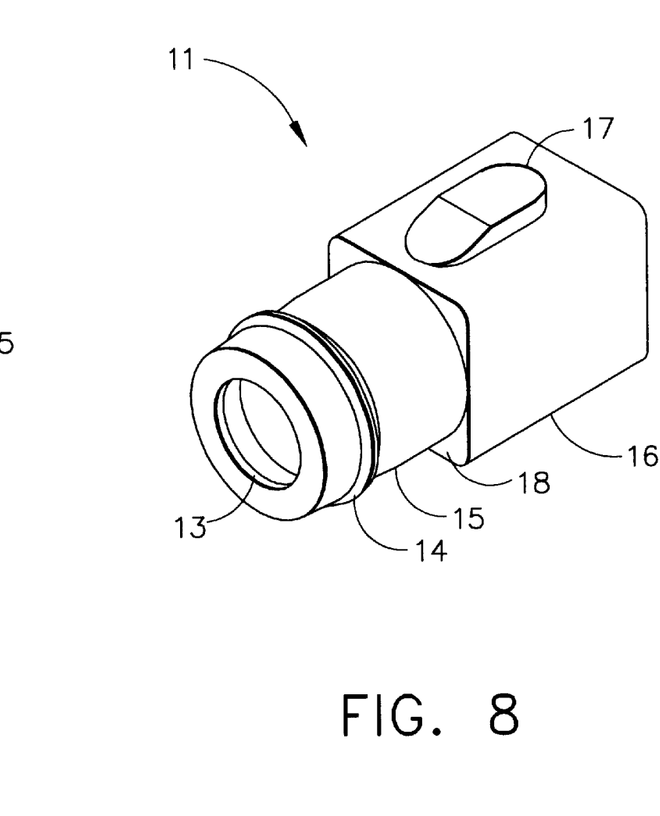
FIG. 8 is an isometric view of a proximal frame seal which inserts into the proximal end of the probe frame of FIG. 4.

FIG. 8 shows the proximal frame seal 11 in an enlarged, isometric view. The proximal frame seal 11 is also shown in FIG. 9 as it is assembled into the proximal end 49 of the frame 40. The proximal frame seal 11 comprises an opening 13, a gland 14, a round portion 15 projecting distally from a proximal surface 18 of a rectangular portion 16. A retention tab 17 projects from the top of the rectangular portion 16 for the elastic insertion into a hole 36 of the frame 40. The proximal frame seal occupies a second radial space 124 defined by the clearance between the cutter tube 53 and the proximal end 49 of the frame 40. The proximal frame seal 11 substantially prevents the flow of fluids through the second radial space.

Both of the frame seals, 1 and 11, the O-rings, 120 and 121, and the proximal cutter seal 114 (see FIG. 3) may be made any of a number of medical grade polymers and elastomers which can withstand gamma radiation and ethylene oxide (ETO) sterilization techniques for disposable medical products. Examples of such materials available are polyethylene, polypropylene, silicone, and polyurethane.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A biopsy probe for the collection of at least one soft tissue ample from a surgical patient, said biopsy probe comprising:

a. a frame having a distal end and a proximal end;

b. an elongated piercing element attached to the distal end of said frame, said piercing element having a piercer lumen, a sharpened distal end for piercing tissue, and a port located proximal to said sharpened distal end for receiving a portion of a tissue mass positioned adjacent to said port, said piercing element and the distal end of said frame defining a first radial space therebetween;

c. an elongated cutter having a proximal end, a distal end, and a cutter lumen therethrough, said cutter being disposed coaxially and slideably relative to said piercing element, said cutter having a cutting blade on said distal end for cutting the portion of tissue protruding into said port of said piercing element when said cutter slides distally past said port, thereby depositing the portion of cut tissue within said cutter lumen of said cutter proximal to said cutting blade, the cutter and the proximal end of said frame defining a second radial space therebetween;

d. a distal frame seal mounted within said first radial space at the distal end of said frame, said distal frame seal adapted to substantially obstruct the passage of fluids through said first radial space between said piercing element and said distal end of said frame;

e. a proximal frame seal mounted within said second radial space at the proximal end of said frame, said proximal frame seal adapted to substantially obstruct the passage of fluids through said second radial space between said cutter and said proximal end of said frame; and f. a tubular tissue remover having a proximal end and a distal end, said remover disposed in said cutter lumen of said cutter and having a structure on the distal end thereof and disposed proximally of said port, said structure adapted to obstruct said cutter lumen so that the portion of cut tissue severed by said cutter is prevented from moving proximally through said cutter lumen, the tissue remover and the proximal end of said cutter defining a third radial space therebetween; and a proximal cutter seal mounted within said third radial space at the proximal end of said cutter, said cutter seal adapted to substantially obstruct the passage of fluid through said third radial space between the proximal end of said cutter and said tissue remover.

2. The biopsy probe of claim 1, further comprising a valve having proximal and distal ends, the distal end of said valve being attached to the proximal end of said tissue remover and the proximal end of said valve being releaseably attachable to a reservoir for fluid communication from said tissue remover to said reservoir through said valve, wherein the passage of air and fluids through said valve occurs only when the proximal end of said valve is attached to said reservoir.

3. The biopsy probe of claim 1 further comprising a tissue sampling surface disposed between the proximal and distal ends of said frame for the retrieval of the portion of the tissue mass positioned adjacent to said port on the piercing element.

4. The biopsy probe of claim 3 further comprising a tube attached to said frame and in fluid communication with said tissue sampling surface of said frame, said tube providing for the removal of fluids from said tissue sampling surface.

5. The biopsy probe of claim 1 further comprising a positioning wheel rotatably mounted on the proximal end of said frame for the rotation of said piercing element about its longitudinal axis.

6. A biopsy probe for the collection of at least one soft tissue sample from a surgical patient, said biopsy device comprising:

a) a frame having a distal end and a proximal end;

b) an elongated piercing element attached to the distal end of said frame, said piercing element having a piercer lumen, a sharpened distal end for piercing tissue, and a port located proximal to said sharpened distal end for receiving a portion of a tissue mass positioned adjacent to said port, said piercing element and the distal end of said frame defining a first radial space therebetween;

c) an elongated cutter having a proximal end, a distal end, and a cutter lumen therethrough, said cutter being disposed coaxially and slideably relative to said piercing element, said cutter having a cutting blade on said distal end for cutting the portion of tissue protruding into said port of said piercing element when said cutter slides distally past said port, thereby depositing the portion of cut tissue within said cutter lumen of said cutter proximal to said cutting blade, said cutter and the proximal end of said frame defining a second radial space therebetween;

d) a tubular tissue remover having a proximal end and a distal end, said remover disposed in said cutter lumen of said cutter and having a structure on the distal end thereof and disposed proximally of said port, said structure for obstructing said cutter lumen so that the portion of cut tissue severed by said cutter is prevented from moving proximally through said cutter lumen, the tissue remover and the proximal end of said cutter defining a third radial space therebetween;

e) a proximal cutter seal mounted within the third radial space at the proximal end of said cutter, said cutter seal adapted to substantially obstruct the passage of fluid through said third radial space between the proximal end of said cutter and said tissue remover; and f) a valve having a proximal and a distal end, wherein the distal end of said valve is attached to the proximal end of said tissue remover and the proximal end of said valve is releaseably attachable to a reservoir for fluid communication from said tissue remover to said reservoir through said valve, wherein the passage of air and fluids through said valve occurs only when the proximal end of said valve is attached to said reservoir.

7. The biopsy probe of claim 6, further comprising a distal frame seal mounted within the first radial space at the distal end of said frame, said distal frame seal adapted to substantially obstruct the passage of fluids through the first radial space between said piercing element and the distal end of said frame.

8. The biopsy probe of claim 7, further comprising a proximal frame seal mounted within the second radial space at the proximal end of said frame, said proximal frame seal adapted to substantially obstruct the passage of fluids through the second radial space between said cutter and the proximal end of said frame.

9. The biopsy probe of claim 6, further comprising a tissue sampling surface disposed between the proximal and distal ends of said frame for the retrieval of the portion of the tissue mass positioned adjacent to said port on the piercing element, and a second tube attached to said frame and in fluid communication with said tissue sampling surface of said frame, said second tube providing for the removal of fluids from said tissue sampling surface.

10. The biopsy probe of claim 6, further comprising a positioning wheel rotatably mounted on the proximal end of said frame for the rotation of said piercing element about its longitudinal axis.

* * * * *